(12) United States Patent
Lock

(10) Patent No.: US 7,944,220 B2  
(45) Date of Patent: May 17, 2011

(54) MOISTURE CONTENT SENSOR AND RELATED METHODS

(75) Inventor: Gary Lock, Middlesex (GB)

(73) Assignee: Delta-T Devices Limited, Cambridge (GB)

(*) Notice: Subject to any disclaimer, the term of this patent is extended or adjusted under 35 U.S.C. 154(b) by 579 days.

(21) Appl. No.: 11/722,059

(22) PCT Filed: Dec. 19, 2005

(86) PCT No.: PCT/GB2005/004886  
§ 371 (c)(1), (2), (4) Date: Apr. 14, 2008

(87) PCT Pub. No.: WO2006/064266  
PCT Pub. Date: Jun. 22, 2006

(65) Prior Publication Data  
US 2008/0211521 A1 Sep. 4, 2008

(30) Foreign Application Priority Data

Dec. 17, 2004 (GB) .................................. 0427659.8

(51) Int. Cl.  
G01R 27/08 (2006.01)  
G01R 27/26 (2006.01)

(52) U.S. Cl. ...................................... 324/694; 324/664

(58) Field of Classification Search .................. 324/694, 324/693, 691, 649, 600, 634, 643, 689, 640, 324/664; 73/29.01, 73, 24.04, 25.04  
See application file for complete search history.

(56) References Cited

U.S. PATENT DOCUMENTS 3,911,435 A * 10/1975 Mardon et al. ................. 342/351  
4,909,070 A * 3/1990 Smith ............................... 73/73  
5,397,994 A * 3/1995 Phare ............................ 324/668  
5,424,649 A 6/1995 Gluck et al.  
(Continued)

FOREIGN PATENT DOCUMENTS

DE 10261138 A1 6/2004  
(Continued)

OTHER PUBLICATIONS

J. Balendonck et al., "Application of an Intelligent Dielectric Sensor for Soil Water Content, Electrical Conductivity and Temperature", IMTC 2001, Proceedings of the 18th EEE Instrumentation and Measurement Technology Conference, Budapest. Hungary, May 21-23, 2001 (May 21, 2001), pp. 1817-1822, XPO10547266, ISBN: 0-7803-6646-8.

(Continued)

Primary Examiner — Hoai-An D Nguyen  
(74) Attorney, Agent, or Firm — David W. Carstens; Steven H. Washam; Carstens & Cahoon, LLP

(57) ABSTRACT

A moisture content sensor for measuring the moisture content of a medium. The sensor includes a probe that injects an electrical signal into the medium. Complex impedance circuitry located between the probe and the electrical signal source allows sensing electronics to generate a signal that represents the moisture content within the medium based on changes in the permittivity of the medium. The complex impedance circuitry minimizes the influence of temperature and conductivity of the medium on the sensed signal. The sensing electronics may be adjusted to optimize the sensor for varying medium conditions and to vary the linearity of the response curve based on volumetric water content of the medium.

20 Claims, 5 Drawing Sheets

U.S. PATENT DOCUMENTS

| | | | | |
|---|---|---|---|---|
| 5,452,674 | A | * | 9/1995 | Melville et al. ............... 114/122 |
| 5,459,403 | A | * | 10/1995 | Kohler et al. ................. 324/643 |
| 5,672,976 | A | | 9/1997 | Egger et al. |
| 5,757,197 | A | | 5/1998 | O'Neill |
| 5,804,976 | A | | 9/1998 | Gaskin |
| 5,859,536 | A | | 1/1999 | Stockton |
| 6,104,200 | A | * | 8/2000 | Hook .......................... 324/643 |
| 6,239,601 | B1 | * | 5/2001 | Weinstein ..................... 324/662 |
| 6,281,801 | B1 | | 8/2001 | Cherry et al. |
| 6,553,813 | B2 | * | 4/2003 | Rynhart et al. ................... 73/73 |
| 2004/0038656 | A1 | * | 2/2004 | McCall et al. ................ 455/138 |

FOREIGN PATENT DOCUMENTS

| | | |
|---|---|---|
| ES | 2143411 A1 | 5/2000 |
| FR | 2654834 A1 | 5/1991 |

OTHER PUBLICATIONS

J. Balendonck, Max Hilhorst, "WET-sensor Application note", Report Nr. 2001-07, Mar. 30, 2001, pp. 1-38, XP-002371436.

\* cited by examiner

MOISTURE CONTENT SENSOR AND RELATED METHODS

FIELD OF THE INVENTION

This invention relates to a moisture content sensor and preferably, but not exclusively, to a water content sensor for the measurement of water content in a substrate/medium. In a particular embodiment the moisture content sensor is used to measure the water content in soil. The invention also relates to related methods.

BACKGROUND OF THE INVENTION

It is convenient to describe the background of this idea in relation to the measurement of soil water content but the invention has wider applicability. For example the moisture content sensor may be used in any of the non-exhaustive list of substrates and/or mediums: cotton wool, mineral wool, sand, rock-wool, volcanic material, plant growing media, concrete, building material, pharmaceutical materials and the like. Further, the moisture content sensor may also find application for measuring in the, non-exhaustive, list of applications: environmental monitoring, irrigation monitoring, irrigation control, crop yield optimisation, flood control, damp measurement, building subsidence, refuse compost monitoring and drug manufacturing in the pharmaceutical industry.

Measuring soil moisture content is non-trivial and complex with a number of well known problems in order to measure to any level of accuracy and reproducibility. This is in part due to soil non-homogeneity and variation of soil composition, but also largely due to other environmental and soil conditions. Most crops are grown in soil with a salinity and nutrient level corresponding to an electrical conductivity between 60 mS/m to 400 mS/m (0.6 dS/m to 4 dS/m). This value can be as low as 20 mS/m and as high as 500 mS/m to 600 mS/m for certain crops, such as tomatoes, with soil conductivity in coastal environments up to 3,000 mS/m. With pressure on food production worldwide crops are increasingly being grown in arid and semi-arid regions, many of which have an indigenous salinity problem. At the same time in many areas salinization is on the increase every year because of indiscriminate use of ground water and poor drainage facilities. In many environments temperature can vary noticeably over a 24 hour period, varying as much as 40 degC in some cases. For soil moisture content sensors used in monitoring and control applications there are further application considerations such as moisture content sensor response time and hysteresis in sensor response.

Variation in soil salinity and nutrients can cause errors, which may be significant, in estimated soil water content. To further add to the complexity of accurate soil moisture measurement the conductivity of the soil is temperature dependant and as such if a moisture content sensor has significant salinity response, and there is a temperature change, then the moisture content sensor will be affected. The affect will generally manifest itself as an apparent temperature sensitivity error, resulting from the salinity response of the moisture content sensor.

Dielectric soil moisture content sensors address a number of the application and accuracy issues of other sensing technologies, offering reproducible readings between different moisture content sensors and benefiting from a rapid response time, with no hysteresis in response for rapidly wetting or drying soil. The performance of a dielectric moisture content sensor is however commonly limited by sensitivity to salinity and nutrient levels in the soil, as well as sensitivity to temperature change.

There are a number of known techniques for measuring soil water content. The Neutron probe has been widely used but such apparatus is expensive and since they include radioactive material they increasingly face regulatory burdens including the requirement that they cannot be left unattended. Such expense and regulatory requirements reduce their usefulness for applications such as irrigation. Neutron probes have also been found to be inaccurate in the top 15 cm of the soil. This region is of particular interest for shallow rooted plants and in particular a large number of commercially grown shallow rooted crops.

Matric potential sensors measure soil matric potential rather than volumetric water content of the soil. Soil moisture is transferred to the matric material from the soil and the electrical resistance of the matric material is in turn measured. Matric potential sensors are commonly made from gypsum and are low cost but have slow response times, significant hysteresis, and commonly have a short life-span (particularly in highly acidic soil where they can last less than 1 season). Typically there is significant variance between differing sensors and calibration is complex, with sensors commonly un-calibrated with poor absolute accuracy, and as such are commonly used for monitoring trends rather than absolute soil properties. Slow response time and hysteresis limit a sensors application in certain soils, particularly sandy soils, where a wetting front can rapidly pass through the soil. Similarly this can limit their application in irrigation control where a fast response to soil changes can be needed.

Tensiometers measure soil tension, a measure of how easy it is for plants to take moisture from the soil. Tensiometers are typically water filled and require regular maintenance.

TDR (Time Domain Reflectometry) works by measuring the time propagation of an electromagnetic wave through the soil. This technique can be less accurate in some soils, such as fine particle soils, and can require complex and expensive electronics to implement.

U.S. Pat. No. 5,424,649, discloses a moisture content sensor with probes that have a thin dielectric coating. Such an arrangement desensitises the sensing electronics to an extent from soil conductivity. The electronics used in this moisture content sensor are highly sensitive to soil conductivity, necessitating the use of a dielectric barrier between the sensing electronics and the soil. A dielectric coating is only partially effective at reducing sensitivity to soil conductivity which results in a moisture content sensor with sensitivity to soil conductivity and salinity. The arrangement is such that the dielectric barrier needs to be thin in order to achieve a level of sensitivity (a thickness of 0.05 mm is outlined). This results in probes that are not robust, limiting the applications in which the moisture content sensor may be used reliably.

Another prior art example is U.S. Pat. No. 5,859,536 which discloses a moisture content sensor using two impedance matching networks, with the two networks used to match the impedance of the soil medium to that of an oscillator source impedance. The disclosed arrangement measures a rectified signal on the output side of the matching circuits, directly at the probe inserted in the media. Such an arrangement is found to offer limited insensitivity to the conductance of soil.

Another prior art example is U.S. Pat. No. 5,804,976 which discloses a dielectric moisture content sensor that utilises a probe arrangement inserted in the soil, and a transmission line. The probe arrangement and transmission line are arranged such that the impedance of the soil in the probe arrangement is nominally matched to that of the transmission line. A signal is injected into the soil. If the impedance of the transmission line is mismatched from that of the probe then a proportion of the signal will be reflected. Reflections from the injected signal are used to determine the volumetric water content of the soil. Such arrangement measures two signals, one of which is on the output side of the moisture content sensor and so is still susceptible to variation in the conductance of soil, noticeable at high volumetric water content, which can be a particular issue when used in artificial growing substrates, such as mineral wool or rockwool.

In arrangements that use impedance matching to match the impedance of the soil and measure the signal directly at the probe inserted in the soil or other medium, in the range of conditions commonly found in agricultural soils, it is likely that, even at high frequencies such as 100 MHz, the signal will be significantly influenced by ionic content of the moisture being measured (due to nutrients, salt, fertiliser, etc.), particularly at high volumetric water content, which is undesirable.

The transmission properties of the soil are dependent upon a range of factors including whether there are any impurities within the soil, the temperature of the soil and even the constitution of the soil itself. For example, if there are impurities in the soil then the conductance of the soil may vary significantly and the moisture content sensor should preferably be arranged to be insensitive to such conductance variations. It is therefore a problem to produce a moisture content sensor that provides the water content of soil accurately across a range of conditions that may be experienced.

SUMMARY OF THE INVENTION

According to a first aspect of the invention there is provided a moisture content sensor comprising a signal source arranged to provide a signal, a probe arranged to inject the signal into a medium in which the moisture content is to be measured, a complex impedance placed between the probe and the signal source and sensing electronics arranged to monitor the signal at a point between the signal source and the complex impedance and generate a primary measurement therefrom which is indicative of the moisture content of the medium.

Such an arrangement is advantageous because it can be arranged such that it is not, or is less, influenced by the conductance of the soil which can vary greatly depending on whether there are impurities present. As such the method may be more accurate than prior art methods. Further, it will be appreciated that embodiments of the present invention allow the moisture content, sometimes referred to as the volumetric moisture content, to be derived from the primary measurement without reference to other measurements.

Preferably, the complex impedance is arranged such that it makes the signal monitored by the sensing electronics sensitive to changes in medium permittivity but insensitive to changes in medium conductivity. Such an arrangement is advantageous because the conductivity of the medium can be greatly affected by impurities such as salts, fertilisers and the like and it is therefore desirable to be able to measure water content irrespective of the presence of these impurities. A further advantage of such an arrangement is that conductivity of a medium is dependent upon temperature. Therefore, arranging the complex impedance such that the sensed signal is insensitive to medium conductivity also minimises sensitivity to temperature.

Further, the sensing electronics may be adjustable. Such an arrangement is convenient because it allows the moisture content sensor to be selectively optimised for varying medium conditions. In the example of the medium being soil, it may be possible to have a moisture content sensor optimised for sandy and/or clay soil, or the like, or similarly optimised for growing media such as rockwool. It may be possible to arrange the electronics to selectively choose a point in the response, corresponding to a volumetric water content value, at which errors due to medium salinity or nutrient content approach zero.

It may be also possible to arrange the electronics such that they can be adjusted such that the linearity of the moisture content sensor's response is made more or less sensitive at high or low volumetric water content. The electronics may, for example, be arranged to make errors due to medium salinity or nutrient content approach zero in the region of the response of most interest for a predetermined application, whilst also minimising errors over the full medium moisture range.

Similarly the electronics may be arranged such that moisture content sensor's sensitivity may be adjusted to match the specific needs of an application, for example a dielectric tensiometer. In such an embodiment a known ceramic material may be placed between the sensing electrodes and the moisture content of the ceramic measured. When the sensor and ceramic are placed in soil, for example, the ceramic will draw moisture from the soil with the moisture content of the ceramic being indicative of how easy it is for a plant to draw moisture from the soil. A ceramic material will typically have a highly non-linear water release curve and by means of an embodiment of the invention it is possible to arrange the electronics so as to produce a sensor with more linear response and significantly improved sensitivity, extending the usable and sensitive range. A dielectric tensiometer offers benefits over water filled tensiometers, producing a tensiometer which needs little or no maintenance.

The moisture content sensor may be arranged such that the medium to measure the moisture content of is soil. However, the moisture content sensor may be arranged to measure other mediums. A non exhaustive list of mediums and/or substrates that the moisture content sensor may be used to measure has already been outlined, including: expanded volcanic material, cotton wool, sand, mineral wool, concrete, building materials, seeds, plant matter, compost.

The oscillator may be arranged to generate the signal at substantially only a single frequency.

The oscillator may be arranged to generate signals in roughly the following range 10 MHz to 1 GHz. More preferably, the oscillator may be arranged to generate signals in roughly the following range 50 MHz to 300 MHz. In perhaps the most preferred embodiment the oscillator is arranged to generate signals at roughly 100 MHz. Such frequencies are advantageous because, to an extent, they help to reduce the effect of the conductance of the medium on measurements taken by the moisture content sensor. The skilled person will appreciate that conductivity of the soil relates to the resistance of the soil and the permittivity of the soil relates to the capacitance of the soil. The effective impedance of a capacitor reduces with increased frequency, thus using high frequencies, in part, increases sensitivity to soil capacitance relative to sensitivity to the soil conductance.

Conveniently, the sensing electronics is arranged to monitor the amplitude of the signal. Such an arrangement is desirable compared to detecting changes in soil moisture content from changes in signal frequency, as is utilised in much prior art. Detecting changes in soil moisture content from changes in signal amplitude, rather than signal frequency, permits lower cost and lower complexity electronics to convert detected soil moisture into a corresponding output voltage signal. It also permits implementation of different medium sensing arrangements.

The sensing electronics may comprise one or more peak detector circuits.

The probe may comprise a conducting pin, generally a metal pin, that is arranged to be inserted into the medium. The pin may be fabricated from stainless steel, which can be desirable for mechanical strength and corrosion resistance. As discussed above, because the moisture content sensor is arranged to be insensitive to changes in soil conductivity it is possible to use mechanically strong probes that are highly conductive, which is not the case in some prior art.

The probe may be arranged so that it may be hammered into the medium. Such an arrangement is advantageous because it would, for example, allow the probe to be inserted into hard and/or stony soil.

However, in other embodiments the probe may be fabricated from a carbon or metal loaded epoxy, or conductive polymer or the like. In further additional, or alternative embodiments, the probe may comprise a conducting pin covered by a dielectric, or use a PCB (Printed Circuit Board) for the probe arrangement. Such arrangements could find merit for manufacturing cost reduction in less mechanically demanding applications or provide application in monitoring extremely high conductivity electrolyte solutions, for example.

The moisture content sensor may also comprise a temperature sensor arranged to determine the temperature of the medium in which the probe is arranged to measure the moisture content. The temperature sensor may be in direct thermal contact with the probe(s) or the medium and/or substrate, or measure the ambient temperature of the moisture content sensor.

The moisture content sensor may be arranged to determine the conductivity of the medium in addition to the moisture content.

In additional embodiments the sensing electronics may also be arranged to monitor the signal at a point between the complex impedance and the probe and generate a secondary measurement. In such embodiments the signal (and therefore the secondary measurement) between the probe and the complex impedance will be more sensitive to the conductivity of the medium and the complex impedance may be arranged such that the signal (and therefore the primary measurement) between the complex impedance and the oscillator is sensitive to the permittivity of the medium and insensitive to the conductivity of the medium. If the embodiment further comprises a temperature sensor then water content, conductivity and/or salinity or nutrients, and temperature of a medium may also be measured.

In a further embodiment the sensing electronics are arranged such that they measure the phase and amplitude of the signal. In this embodiment the medium permittivity and moisture content, as well as conductivity and/or salinity may be measured, with the signal amplitude being more sensitive to the medium conductivity and signal phase more sensitive to the medium permittivity. In this embodiment it is desirable to also measure temperature. As such a moisture content sensor is provided that is able to measure temperature, permittivity, moisture content, conductivity and/or salinity of a medium and/or substrate.

In a further alternative embodiment the complex impedance is arranged such that the signal between the complex impedance and the oscillator is insensitive to conductivity and sensitive to permittivity of the medium. In this embodiment the sensing electronics are arranged such that they measure the phase of the signal, with a further embodiment measuring both phase and amplitude. Temperature may also be measured.

As a further embodiment the oscillator may be arranged to generate more than one frequency. The moisture content sensor may be arranged to either apply the frequencies at the same time or sequentially. If more than one frequency is utilised it may be preferable to apply signals of substantially different frequencies and it is perhaps beneficial for signals to be separated by at least a decade. Preferably at least one signal is applied at a frequency in roughly the range 50 MHz to 300 MHz. Such an arrangement may be beneficial to measure medium conductivity as well as medium moisture.

The moisture content sensor may comprise a plurality of any of the following: probes, sensing electronics, complex impedances. In such embodiments the probes may be longitudinally spaced from one another along a support means. Such arrangements are advantageous since they may provide a single moisture content sensor that is able to be inserted into a medium and/or substrate to produce a moisture profile at different depths of the medium. Such a moisture content sensor finds particular application in agriculture to measure a soil moisture profile over and below a crops root depth. This is particularly valuable and insightful in determining if a plant needs water and when to irrigate. As outlined an moisture content sensor may also be produced that provides moisture, temperature, conductivity, salinity, and/or nutrient profiles, or any combination there of.

Such moisture content sensors may be directly inserted in the medium with sensing pins in direct electrical contact with the medium, or else coupled through an access tube that may be plastic, fibreglass, Kevlar, or the like. The benefit of utilising an access tube is convenience, allowing an instrument to easily be removed from the medium as well as allowing a moisture content sensor to be used to measure profiles at multiple sites and/or multiple installations. An access tube will typically be of 20 mm or greater diameter, and may preferably be of 35 mm to 50 mm diameter or greater. For application in agriculture the access tube can be of a length typically from roughly 0.5 meters up to roughly 2 meters but, can be roughly 3 meters or longer, thus allowing a profile to be measured over and below the root zone of a crop.

As a further variant a moisture and/or conductivity, salinity, nutrient temperature profile may be measured with an instrument using a single probe. In this case the probe is moved along the length of an access tube and measurements taken in differing positions, thus permitting a profile to be measured along the length of the access tube.

According to a second aspect of the invention there is provided a method of measuring the moisture content of a medium comprising injecting a signal produced by an signal source, through a complex impedance and a probe into the medium, monitoring the signal at a point between the signal source and the complex impedance in order to generate a first measurement which is indicative of the moisture content of the medium.

According to a third aspect of the invention there is provided a moisture content sensor comprising a signal source arranged to provide a signal, a probe arranged to inject the signal into a medium in which the moisture content is to be measured and sensing electronics wherein the sensing electronics is arranged to generate a primary measurement of the signal indicative of the moisture content of the medium and a secondary measurement indicative of the ionic content of the moisture.

The ionic content may be used to determine factors about the moisture such as the amount of salt, the amount of nutrients, etc. therein.

According to a fourth aspect of the invention there is provided a moisture content sensor comprising a signal source arranged to provide a signal, a probe arranged to inject the signal into a medium in which the moisture content is to be measured, a complex impedance placed between the probe and the signal source wherein the complex impedance together with an impedance provided by the medium in which the probe is, in use, inserted form an element of a potential divider, the other element being provided by a sensing impedance, the sensor also comprising sensing electronics arranged to sense the signal at a point between the sensing impedance and the complex impedance.

According to a fifth aspect of the invention there is provided a moisture content sensor comprising a signal source arranged to provide a signal, a probe arranged to inject the signal into a medium in which the moisture content is to be measured, a complex impedance, provided in the form of a PI circuit, placed between the probe and the signal source and sensing electronics arranged to monitor the signal at a point between the signal source and the complex impedance and generate a primary measurement therefrom which is indicative of the moisture content of the medium.

According to a sixth aspect of the invention there is provided a moisture content sensor comprising a signal source arranged to provide a signal at substantially a constant frequency, a probe arranged to inject the signal into a medium in which the moisture content is to be measured, a complex impedance placed between the probe and the signal source and sensing electronics arranged to monitor the signal at a point between the signal source and the complex impedance and generate a primary measurement therefrom which is indicative of the moisture content of the medium.

The features discussed in relation to any of the aspects of the invention may be applied to any other of the aspects of the invention.

BRIEF DESCRIPTION OF THE DRAWINGS

There now follows by way of example only a detailed description of the present invention with reference to the accompanying drawings in which.

DETAILED DESCRIPTION OF THE DRAWINGS

Figure 1:
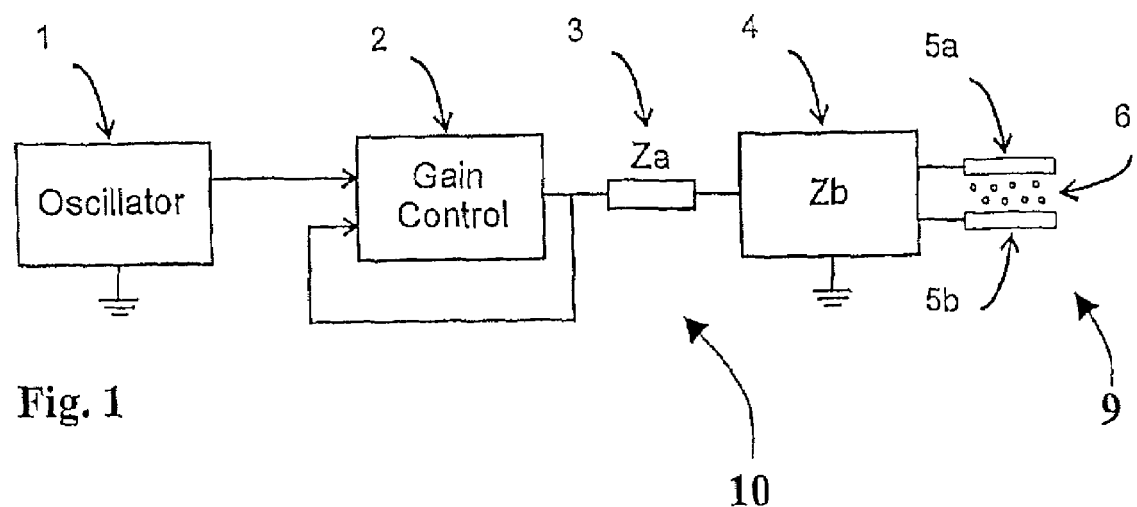
FIG. 1 and FIG. 2 show a simplified equivalent circuit for the circuits of FIGS. 3 to 5.

FIG. 1 shows a schematic of the sensing circuitry 10 used in providing a moisture content sensor according to embodiments of the present invention. The medium 6 that is being measured is in this embodiment soil. A detector circuit in the moisture content sensor provides a complex impedance which may be referred to as an impedance $Z_b$. It will be appreciated that a complex impedance is an impedance which has a real and an imaginary component; i.e. it has a resistive element as well as an element provided by one or both of a capacitor and an inductor.

A probe is inserted into the medium and is then connected to the sensing circuitry 10 with the medium volume enclosed within the sensing field of the probe having a medium impedance $Z_{medium}$. The probe is represented by the two pins 5a and 5b in FIG. 1 and various pin and other probe arrangements are discussed hereinafter.

An oscillator (also know as a signal generator) 1 is arranged to generate a high frequency signal, typically a sine wave. In this embodiment the signal is at roughly 100 Hz but the skilled person will appreciate that other frequencies may also be suitable. The signal is fed to the pins 5a and 5b. It will be appreciated that the oscillator 1, the complex impedance 4 and the probe 5a, 5b are arranged in series with one another.

Further, it will be seen that the sensing circuitry 10 comprises a gain control loop 2, which produces a stabilised signal generated by the oscillator 1. A further advantage of using a gain control loop 2 is that the oscillator 1 is isolated and its output compensated for temperature and load changes, ensuring the signal injected into a sensing impedance $Z_a$ is stable and controlled.

Figure 3:
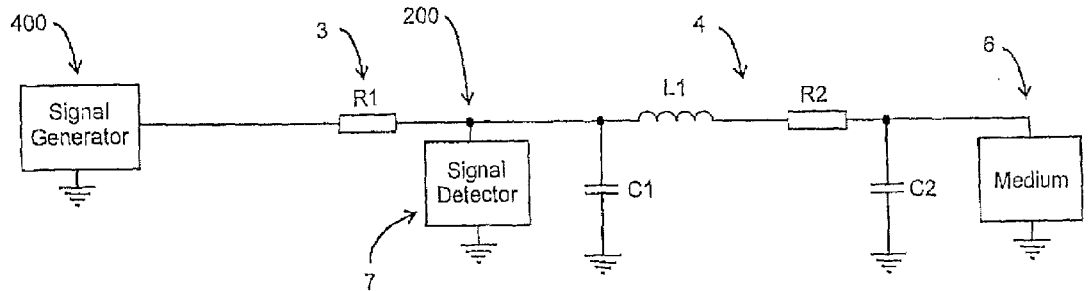
FIG. 3 schematically shows a circuit according to a first embodiment of the invention.
Figure 4:
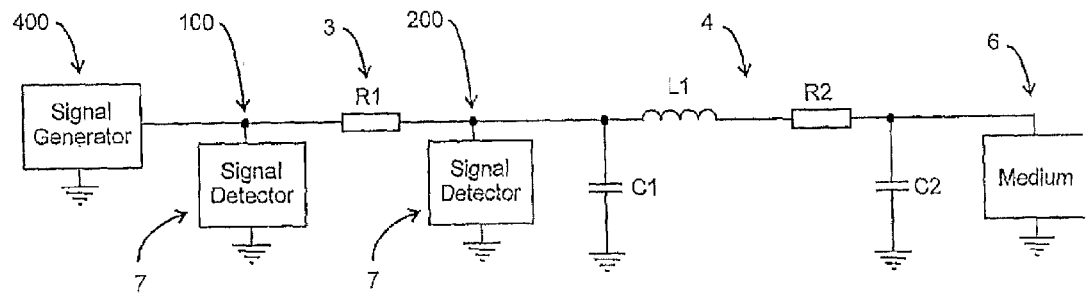
FIG. 4 schematically shows a circuit according to a second embodiment of the invention.
Figure 5:
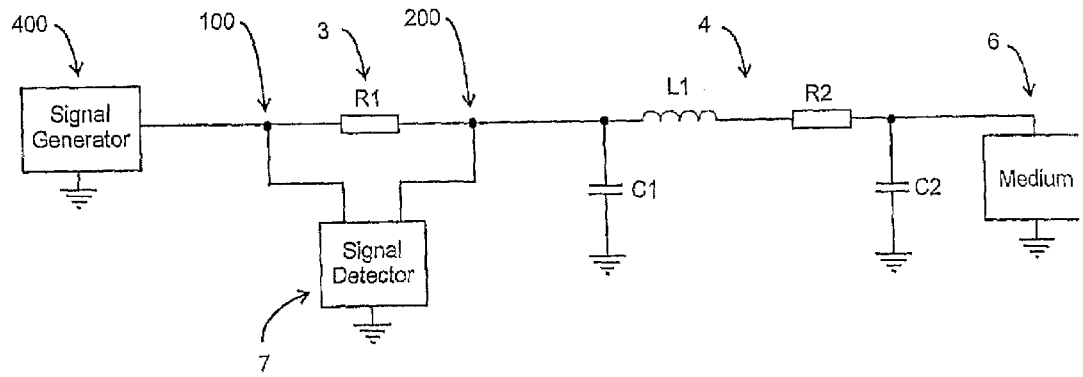
FIG. 5 schematically shows a circuit according to a third embodiment of the invention.

The sensing impedance $Z_a$ 3 is connected in series between the oscillator 1 and the complex impedance $Z_b$ 4 and allows an output to be taken from the circuit. FIGS. 3, 4 and 5 show various arrangements for connecting a signal detector 7 (which may constitute sensing electronics).

Figure 2:
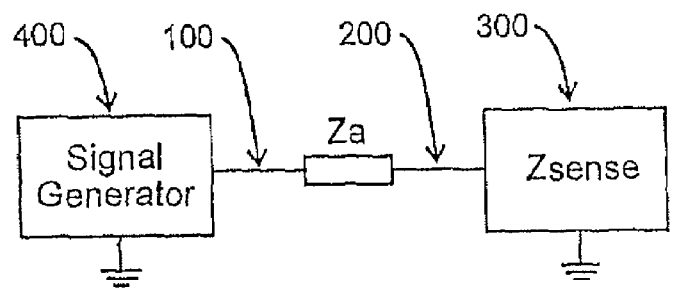

FIG. 2 shows a schematic of the sensing circuitry. A signal generator 400 is arranged to generate a signal such that the signal at 100 is an amplitude and frequency stable signal irrespective of any temperature or electrical load changes. $Z_{sense}$ 300 corresponds to the combined impedance of the detector circuit 4 and the medium 6.

Embodiments of the invention may be arranged to have a low temperature response; i.e. the moisture content generated by the sensor is stable regardless of temperature changes. Temperature dependence of a response can arise due to a sensor's influence by ions in the moisture (i.e. salinity response) and the temperature dependence of this salinity response. Such an advantage occurs by tailoring of the components within the complex impedance $Z_b$. Thus, in some embodiments it is possible to remove a temperature sensor which can reduce the costs of the moisture sensor.

Referring back to FIG. 1, pins 5a and 5b inserted in medium 6 will generate a radio frequency electromagnetic field. The generated electromagnetic field will encompass a volume of the medium 6, corresponding to the sensing field of the probe, with this volume of medium having an impedance $Z_{medium}$. The impedance $Z_{medium}$ will interact with the complex impedance 4 (of impedance $Z_b$) giving a resulting impedance $Z_{sense}$ 300, as shown in FIG. 2.

The complex impedance 4 is preferably arranged such that the signal between the complex impedance 4 and the oscillator 400 (and in particular between the complex impedance 4 and the impedance $Z_a$) is sensitive to the capacitance component of $Z_{medium}$ but highly insensitive to the resistance component of $Z_{medium}$. This results in an impedance $Z_{sense}$, an impedance that is sensitive to the moisture content of the medium 6, but is insensitive to the conductivity of the medium 6. As the skilled person will appreciate impedances $Z_a$ and $Z_{sense}$ may be arranged such that they form a potential divider.

A change in moisture content of the medium will result in a corresponding change in $Z_{sense}$ with the signal amplitude at a point between $Z_a$ and $Z_{sense}$ 200 corresponding to the moisture content of the medium and insensitive to medium conductivity.

Figure 11:
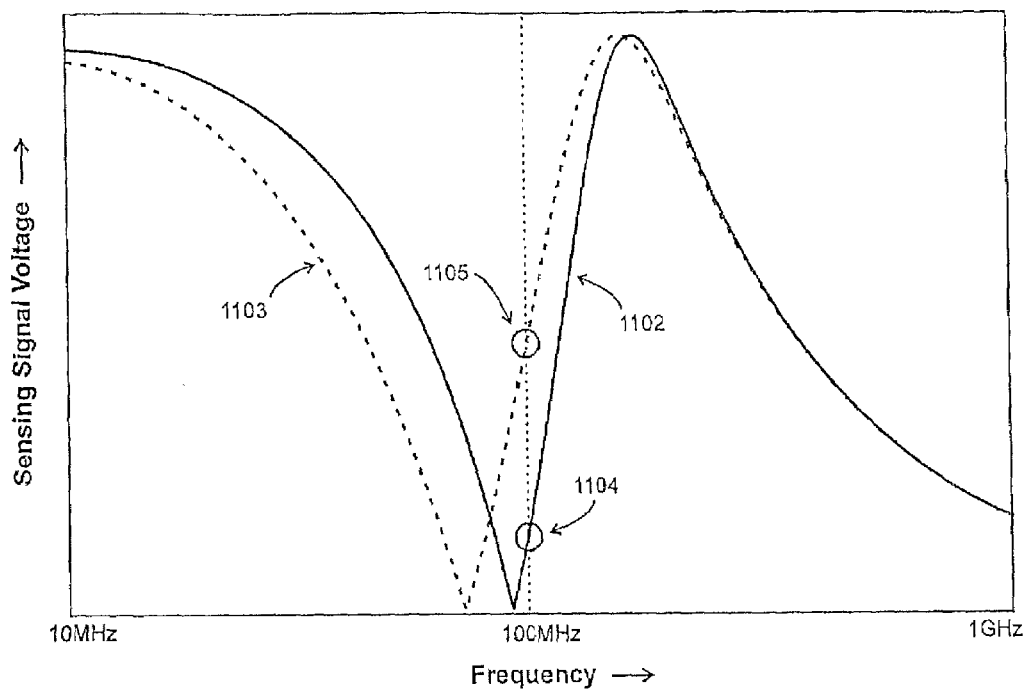
FIG. 11 shows a possible frequency response for an embodiment of the present invention.

FIG. 11 shows an example frequency response for the detector circuit arrangement $Z_a$ and $Z_{sense}$. An increase in the moisture content of the medium corresponds to an increase in the capacitance of $Z_{medium}$. An increase in capacitance of $Z_{medium}$ in turn results in a negative relative frequency shift in the impedance response of $Z_{sense}$. With a fixed 100 MHz signal applied, for example, this has the effect of increasing the effective impedance of $Z_{sense}$. The solid plotted response 1102 in FIG. 11 corresponds to the signal voltage at the point between $Z_a$ and $Z_{sense}$ 200 (in FIG. 2) with a medium of low moisture content. The dashed response 1103 corresponds to a medium of much higher moisture content. Any increase or decrease in the moisture content of the medium has a corresponding effect on the signal amplitude at the point between $Z_a$ and $Z_{sense}$ 200.

FIG. 3 shows a single signal detector 7 placed between the sensing impedance $Z_a$ 3 and the complex impedance $Z_b$ 4 (i.e. between the complex impedance 4 and the signal generator). In FIGS. 3, 4, and 5 the sensing impedance $Z_a$ is represented by a fixed resistance R1, with the complex impedance 4 represented by the complex impedance of C1, C2, L1, R2, arranged in a Pi-circuit arrangement.

Thus, the circuits shown in the embodiments of FIGS. 3, 4 and 5 are arranged such that a change in the moisture content of the medium 6 results in a corresponding change in the signal at the signal detector 7. In these embodiments, the signal detector 7 is arranged to monitor the signal at a point between the signal source and the complex impedance $Z_b$ 4 and to generate a primary measurement therefrom. Such positioning of the signal detector 7 is advantageous because it provides a simpler and more accurate arrangement than those of the prior art. The impedance of the medium $Z_{medium}$ provides part of the impedance of the potential divider $Z_{sense}$ and $Z_a$ and as such forms part of the circuit providing for a simpler arrangement.

Tailoring the components of $Z_b$ allows the characteristics of the circuit to be optimised. Some embodiments of the circuit may allow the response of the circuit to be tailored for any one or more of the following parameters: ionic content (e.g. salinity/nutrient content); the period over which the response is linear; and the shape of the response curve. Tailoring of these individual response features would not generally be possible in prior art arrangements, such as those relying on impedance matching. The skilled person will appreciate that this tailoring can be achieved by altering the relative values of $Z_a$, $Z_b$, $C_1$, $C_2$ and $L_1$ and he/she will readily appreciate how to model the response in order to tailor the response desired.

Tailoring the characteristics has particular benefit in producing a sensor with low sensitivity to soil conductivity and producing a sensor with a linear response over the full measurement range. In one particular embodiment the probe comprises a ceramic material and the moisture content within the ceramic material is measured. This is often referred as a dielectric tensiometer sensor and allows soil tension to be measured. However, a ceramic material typically has a non-linear water release curve such that its response is non-linear. Such an embodiment of the invention should allow the circuit to be tailored to provide a more linear response, improving measurement accuracy and measurement range, for a given ceramic material. This may similarly applied to tailoring the response to a matric material arranged to measure the matric potential.

Embodiments of the invention in which the response is linearised for a dielectric tensiometer sensor are likely to require less maintenance than prior art sensors. Such maintenance which was generally required in prior art tensiometer sensors has made such sensors costly and as such embodiments of the invention may be particularly beneficial in agricultural applications where it is desirable to use a sensor that does not need significant maintenance.

FIG. 4 shows a further embodiment in which two signal detectors are placed each side of the sensing impedance 3. The signal detector at the point between the complex impedance and the sensing impedance 200 is able detect moisture changes in the medium. The signal detector on the other side of the sensing impedance at a point between the sensing impedance and the oscillator 100 is able to detect changes in the reference signal. The detected signal at the point between the sensing impedance and the oscillator 100 may be used to compensate the signal detected at the point between the complex impedance and the sensing impedance 200. The detected signal at the point between the sensing impedance and the oscillator 100 may also be used as a reference to control the signal from the signal generator 400. Such an arrangement may provide improved accuracy over the arrangement of FIG. 3.

FIG. 5 shows a further embodiment in which a differential signal is measured across the sensing impedance 3. The signal detector 7 may be implemented as a single signal detector, or as two separate signal detectors, similar to shown in FIG. 4, with the signals measured differentially. Measuring a differential signal across the sensing impedance 3 permits improved accuracy, accounting for any variance in the reference signal.

As can be seen from FIGS. 3, 4 and 5 the complex impedance $Z_b$ 4 is arranged in a Pi-circuit arrangement, comprising an Inductor L1 and series resistor R2 with a capacitance C1 and C2 either side connected to ground. The reference Impedance R1 is connected one side of the complex impedance $Z_a$ 4 Pi-circuit arrangement, between C1 and L1 and the probe connected to the other side of the Pi-circuit arrangement, between R2 and capacitor C2.

The complex impedance 4 may be implemented in other arrangements, such as a differential Pi-arrangement, for example, for when applying a differential rather than single ended signal to the medium. In FIGS. 3, 4, and 5 the resistor R2 can be optionally omitted from the electrical circuit, depending on application, or may also be considered as representing the effective series resistance of the inductor L1.

R2 may be optional in embodiments other than those shown in FIGS. 3, 4 and 5. Whether or not a resistor (e.g., R2) is provided a complex impedance will still be provided due to the series resistance provided by L1.

Figure 6:
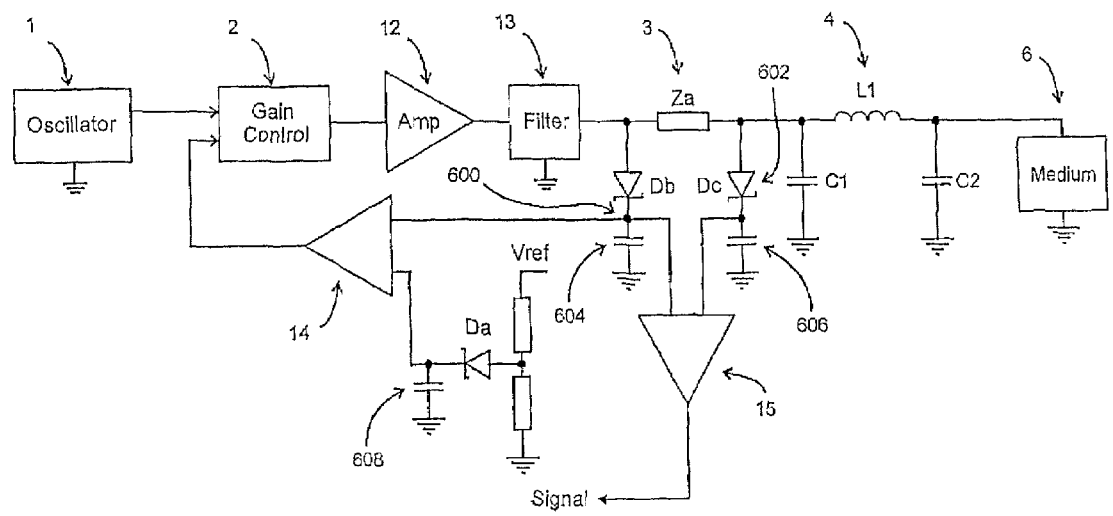
FIG. 6 schematically shows an embodiment of the invention which utilises a gain control loop.

A currently preferred embodiment of the circuit is shown in FIG. 6. It will again be seen that an oscillator 1, a gain control 2, the sensing impedance $Z_a$ 3 and the complex impedance $Z_b$ 4 are all provided.

However, in addition an amplifier 12 is provided and arranged to buffer the signal after gain control 2. A filter 13 is provided after amplifier 12 to ensure a spectrally pure signal is provided to the sensing impedance $Z_a$ 3.

The circuit is equivalent to the circuit of FIG. 5 with a differential signal measured across sensing impedance $Z_a$ 3. In the circuit shown in FIG. 6 the signal detectors 7 are peak detector circuits 600, 602, comprising Schottky diodes $D_b$ and $D_c$ and charging capacitors 604, 606, as will be readily appreciated by the skilled person. The peak detector circuits 600, 602 provide what may be thought of as sensing electronics.

One advantage of providing the complex impedance ($Z_b$) is that it makes the signal at the point between the signal source and the complex impedance ($Z_b$), i.e. point 200 in FIGS. 2 to 5, sensitive to soil moisture content and insensitive to soil salinity. Another advantage of monitoring the signal at point 200 is that it is possible to detect changes in soil moisture content from changes in the amplitude of the signal (for example using the peak detector circuits 600, 602), which provides the possibility of providing a soil moisture content sensor at lower cost. The peak detectors is further advantageous because they help increase the temperature insensitivity of the sensor, the advantages of which are discussed above.

Figure 10:
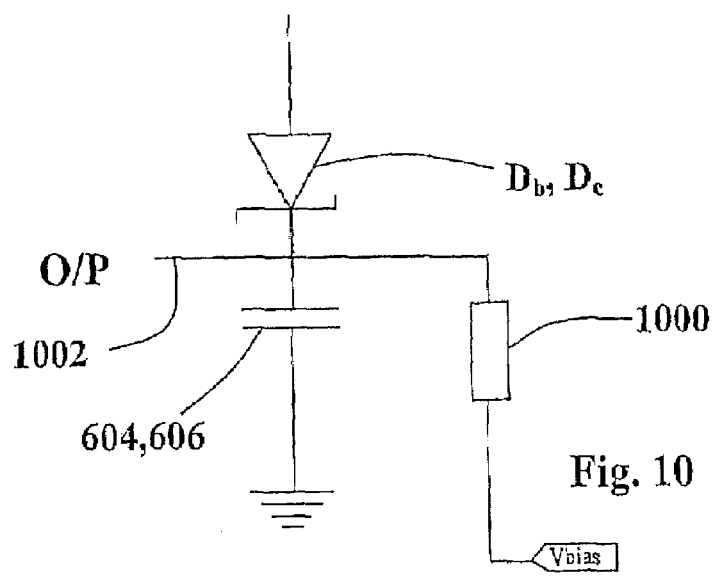
FIG. 10 shows an example of a peak detector circuit.

For reasons of clarity a negatively biased resistor 1000 forming part of the peak detection circuit is not shown in FIG. 6. Some detector diodes do not require negative biasing and so biasing resistor 1000 may not be required. However, an example of a peak detector circuit with negative biasing is shown in FIG. 10. The output 1002 from the peak detector circuit is taken from between the Schottky diode $D_a$, $D_b$, $D_c$ and a capacitor 604, 606, 608 in series therewith.

Referring back to FIG. 6 it can be seen that the outputs 604, 606 from the two peak detector circuits 600, 602 are connected to a differential amplifier 15 which generates an output signal from which the water content of the medium can be determined. Thus, the output of sensing circuit 606 may be thought of as a primary measurement as may the output from the amplifier 15.

It will be seen that the circuit of FIG. 6 shows a third Schotkky diode $D_a$ which is connected in a further peak detector circuit 608. This third diode $D_a$ forms part of the gain control loop which also comprises a differential amplifier 14. The first input of the amplifier 14 is provided by the output of the peak detector 600 and the second input is provided by the output of the peak detector 608. Peak detector diode $D_a$ may be considered as the reference diode as it is biased with a DC voltage, setting the reference level for the gain control loop. Preferably diodes $D_a$, $D_b$, $D_c$ are matched. It will be appreciate that such an arrangement with the gain control loop ensures the electronics are controlled and stabilised irrespective of temperature, environmental or medium conditions and the like.

Selection of the components in the complex impedance 4 allows the behaviour of the moisture content sensor arrangement to be optimised. It is advantageous if the moisture content sensor is not affected by the change of conductance of the medium in which the probe is placed.

By selection of components within the complex impedance 4 it is possible to tailor the circuit such that you may selectively choose a point in the response, corresponding to a volumetric water content value, at which errors due to medium salinity or nutrient content approach zero. By selection of components it is also possible to adjust the linearity of a moisture content sensor's response, for example, making it more or less sensitive at high or low volumetric water content. This high level of flexibility can be advantageous because it allows you to minimise the effects of salinity or nutrients in the soil, for example, and tailor a moisture content sensor's response to the needs of differing applications and differing medium.

FIG. 7 shows various possible probe arrangements that may be used with the circuits of any of the embodiments described above. FIG. 7a shows an arrangement in which the probe comprises two pins 5a and 5b. One of the two pins, in this case 5a, is grounded whilst the signal is applied to the other of the pins 5b. The water in the medium between the two pins modifies the dielectric properties of the medium and thus alters the signal at the sensing electronics 602, 600.

Figure 7A:
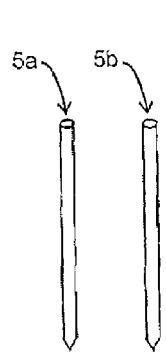
FIG. 7 shows sensing pin arrangements for probes suitable for use with embodiments of the present invention.
Figure 7B:
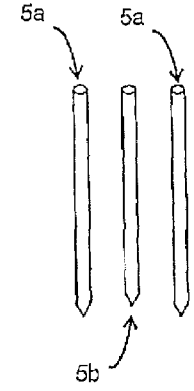

FIG. 7b shows a further arrangement that may be suitable for the probe. In this embodiment there are three pins: the signal is injected into pin 5b and two of the pins 5a are grounded. As will be appreciated with reference to FIGS. 7c and 7d such an embodiment provides a closer approximation to a shielded signal pin 5b than the embodiment of FIG. 7a.

Figure 7C:
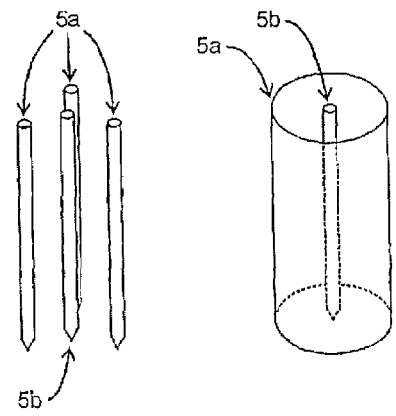

FIG. 7c shows a further possible embodiment of a probe suitable for use with the embodiments described above. In this embodiment there is a single signal pin 5b, but there are three ground pins 5a arranged at roughly 120° intervals around a circle centered on the signal pin 5b. Similar arrangements of four or more outer pins 5a may also be implemented. The arrangement of FIG. 7c can be preferable to the arrangements of 7a or 7b in some applications, offering increased sensitivity and/or increased sensing volume.

Figure 7D:
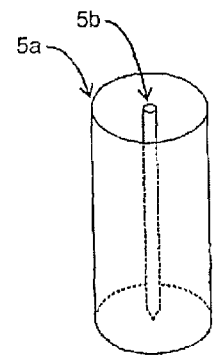

FIG. 7d shows a further embodiment, a so-called co-axial arrangement in which the signal pin 5b is shielded by a tubular conducting earth plane 5a. Pin 5a may have cut-outs or be of a mesh or similar arrangement so as to permit moisture to pass. Other pin arrangements to those of FIG. 7 and variants thereof are clearly possible.

Figures 8, 9:
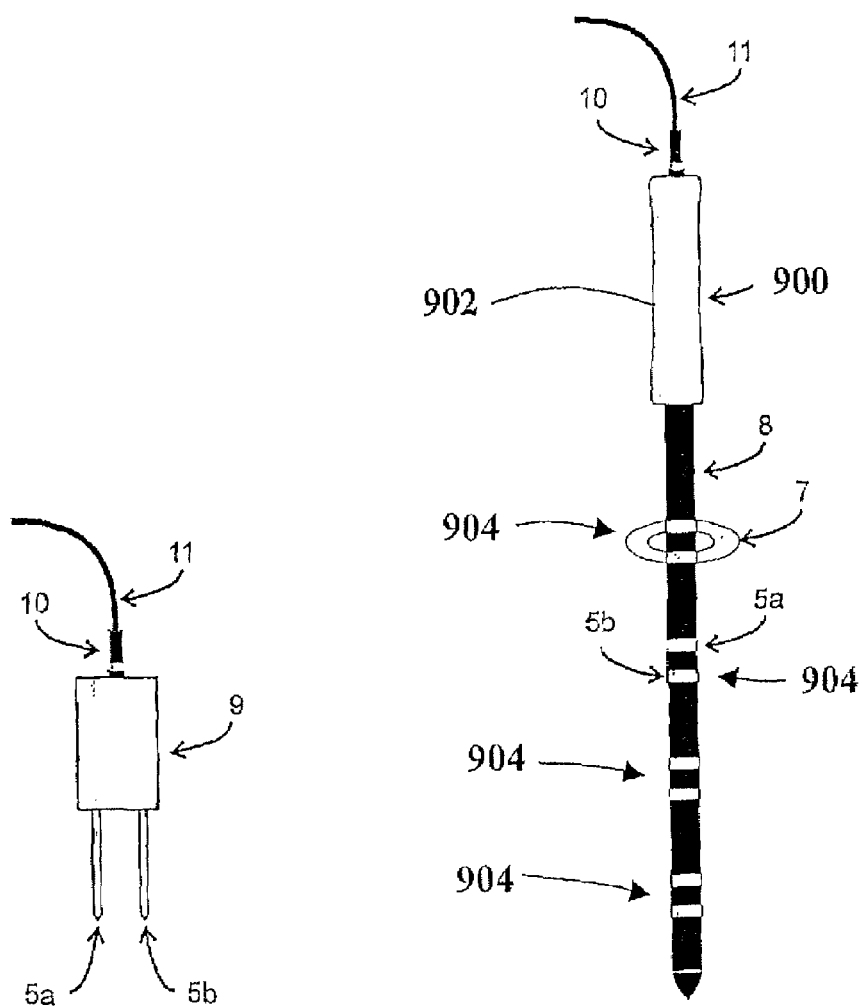
FIG. 8 shows a probe that is used to connect the circuit of FIGS. 1 to 6 and FIG. 12 to a medium.
FIG. 9 shows a probe arrangement used to measure medium properties at multiple points.

FIG. 8 shows a probe 9 which comprises two pins 5a, 5b as in the embodiment of FIG. 7a. The probe 9 is connected via a cable 11, which is connected to the probe 9 with a connector 10, to any one of the embodiments of the moisture content sensor described above. It will be appreciated that a cable may not be used and a wireless (such as infra red, Bluetooth, WiFi, or other radio link) or the like connection may be used. Indeed, in other embodiments the moisture content sensor may be mounted on the probe in what may be termed an embedded embodiment. In such an embedded embodiment data may be logged in a memory for later inspection and/or a display may be provided on the probe allowing a user to view the moisture content.

FIG. 9 shows a further embodiment providing a plurality of probes arranged along a support means 900 that may be used with the embodiments described above. The support means 900 comprises a handle 902 and a shaft 8. At intervals along the length of the shaft 8 there are disposed four pairs of conducting rings 904, with each pair providing a probe. One of the rings of the pair provides a signal pin 5b whilst the other of the rings provides a ground pin 5b. The electric field between the each of the rings in each pair is the sensing field as is shown at 7. The support means may be directly inserted in the medium or coupled through an access tube which permits the support means to be easily inserted and removed from the medium.

Figure 12:
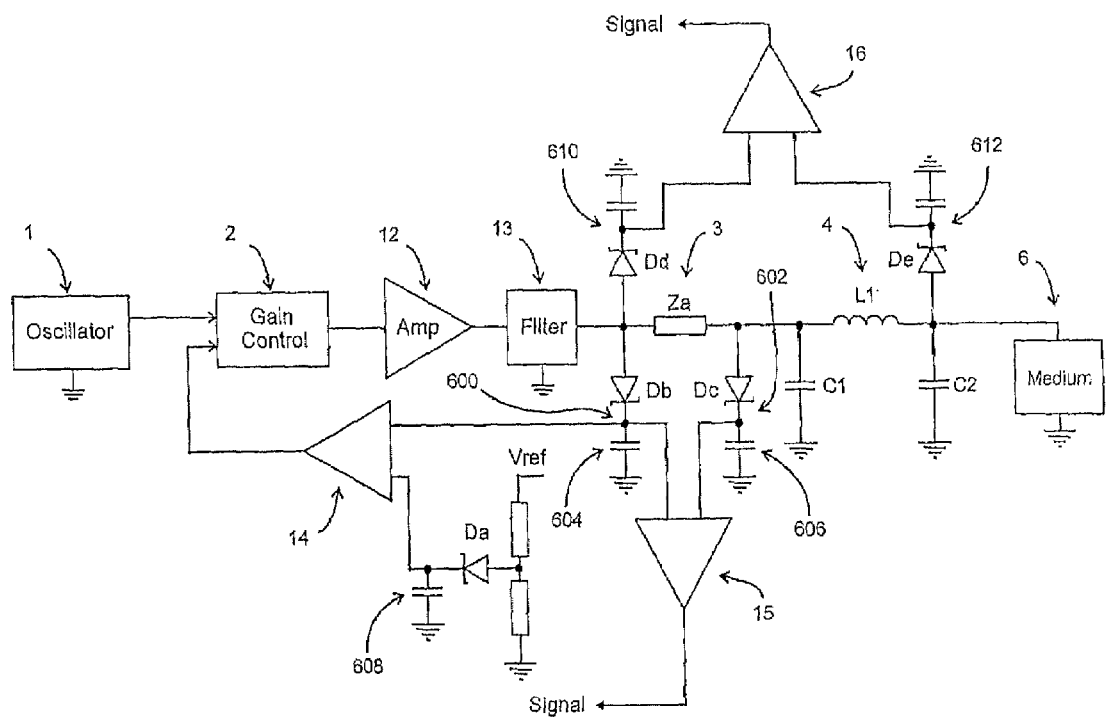
FIG. 12 schematically shows an embodiment of the invention which utilises a gain control loop.

FIG. 12 shows an embodiment that is a variant of FIG. 6. It will again be seen that an oscillator 1, a gain control 2, the sensing impedance $Z_a$ 3 and the complex impedance $Z_b$ 4 are provided, along with the other circuitry outlined in FIG. 6. This embodiment has the addition of measuring the differential signal between the point between the sensing impedance and the oscillator 100 and the output side of the complex impedance 4 (i.e. between the complex impedance 4 and the probe 5a, 5b). Two further peak detector arrangements are shown 610, 612, comprising $D_d$ and $D_e$ with an amplifier 16 measuring the differential signal between the two detected signals which provides a secondary measurement. In this arrangement the complex impedance 4 is arranged such that it is sensitive to the moisture of the medium. The differential signal measured across the sensing impedance $Z_a$ 3, and output by amplifier 15 is therefore sensitive to the moisture content of the medium. The signal on the output side of the complex impedance 4 (i.e. between the complex impedance and the probe) is sensitive to the conductivity of the medium and so the output signal from amplifier 16 is sensitive to the conductivity of the medium. From this medium moisture content as well as medium conductivity may be derived. Preferably a temperature sensor is also incorporated, thus enabling a sensor able to measure moisture, conductivity, and temperature.

In a further embodiment the signal detector 7 of FIGS. 3, 4, and 5, may comprise of a signal detector arrangement that measure the phase of the signal or in a further embodiment both the magnitude and phase of the signal. The arrangements of FIGS. 6 and 12 may utilise similar signal detectors in place of the peak detector arrangements.

In a further embodiment the probe may comprise a single pin arranged to inject the signal into the medium and a ring which is arranged to contact the medium. The ring will generally be grounded and replaces the ground pin 5a of FIG. 7a.

In other embodiments, although not shown in the Figures, the probe may comprise what is know as a matric potential probe. In such an embodiment the pins 5a and 5b, which may be as shown in any of the arrangements of FIGS. 7a to d, are embedded in a matric material such as, gypsum, concrete or fibrous material.

In further embodiments, although not shown in the Figures, the probe may comprise what is know as a dielectric tensiometer. In such an embodiment the pins 5a and 5b, which again may be as shown in any of the arrangements of FIGS. 7a to 7d, are embedded in a ceramic material.

In some embodiments it is possible that the signal that is injected into the medium is generated by an oscillator that is external to the moisture content sensor and connected to the signal source. In other embodiments the signal source may comprise an oscillator.

The invention claimed is:

1. A moisture content sensor, the sensor comprising:
a signal source arranged to provide an a.c. signal;
a probe arranged to inject the signal into a medium in which the moisture content is to be measured;
a complex impedance comprising a PI circuit arrangement provided by a plurality of components including an inductance connected between the first ends of two capacitances provided in parallel with the second ends of the capacitances connected to ground, the Pi-circuit located between the probe and the signal source; and
a sensing impedance placed in series between the complex impedance and the signal source, wherein the sensing impedance and the complex impedance together with the impedance provided by the medium into which the probe is inserted during use form a potential divider; and
sensing electronics arranged to monitor the signal at the junction of the sensing and complex impedances and to generate a measurement of the signal amplitude and/or phase therefrom which is indicative of the moisture content of the medium.

2. A sensor according to claim 1 in which the signal source is arranged to generate the signal at a substantially constant frequency.

3. A sensor according to claim 1 in which the sensing electronics comprises at least one peak detector circuit.

4. A sensor according to claim 1 further comprising a temperature sensor.

5. A sensor according to claim 1, wherein the sensor is arranged to measure at least one of the following properties of a medium: temperature, permittivity, moisture, volumetric water content, conductivity and salinity.

6. A sensor according to claim 1 wherein a plurality of probes are provided and arranged along a support means.

7. A sensor according to claim 6 in which the support means allows a moisture content profile within a medium to be measured.

8. A sensor according to claim 1 wherein a gain control loop is incorporated in or directly following the signal source and arranged to provide an amplitude and/or temperature stabilised signal.

9. A sensor according to claim 1 in which the sensing electronics differentially measures the signal across the sensing impedance in order to generate the measurement.

10. A sensor according to claim 1 which is arranged to generate at least two signals, each at a different frequency, and apply the two signals to the medium via the probe.

11. A sensor according to claim 10 in which the at least two signals are applied sequentially.

12. A sensor according to claim 10 in which the at least two signals are applied at approximately the same time.

13. A sensor according to claim 1 in which the complex impedance is not matched to a nominal impedance of the medium.

14. A sensor according to claim 1 in which the signal source is provided by one of an oscillator within the sensor and a connection to an external oscillator.

15. A sensor according to claim 1 in which the probe comprises a ceramic or other matric material portion and is arranged such that the tension and/or matric potential of the medium surrounding the probe can be determined.

16. A sensor according to claim 15 which is arranged such that the electromagnetic field generated by the probe remains substantially within the ceramic or other matric material portion.

17. A method of measuring the moisture content of a medium, the method comprising:
injecting an a.c. signal produced by a signal source, through a sensing impedance, a complex impedance, each in series with the signal source, and a probe into the medium, the complex impedance being provided by a PI circuit including an inductance connected between first ends of at least two capacitances provided in parallel with the second ends of the capacitances connected to ground, wherein the complex impedance is placed between the probe and the sensing impedance and the sensing impedance is placed between the complex impedance and the signal source, the sensing impedance forming a potential divider with the complex impedance and the impedance provided by the medium in which the probe is inserted; and
monitoring the amplitude and/or phase of the signal at the junction of the sensing and complex impedances to generate a measurement that is indicative of the moisture content of the medium.

18. A method according to claim 17 in which the complex impedance is not matched to a nominal impedance of the medium in which the moisture content is being measured.

19. A method according to claim 17 which also measures any of the following properties of the medium: temperature, permittivity, volumetric water content, conductivity and salinity.

20. A moisture content sensor comprising:
a signal source arranged to provide an a.c. signal;
a probe arranged to inject the signal into a medium in which the moisture content is to be measured;
a complex impedance comprising a Pi-circuit arrangement placed between the probe and the signal source;

a sensing impedance placed in series between the complex impedance and the signal source, wherein the sensing impedance and the complex impedance together with an impedance provided by the medium into which the probe is inserted form a potential divider; and sensing electronics arranged to measure the amplitude and/or phase of the signal at the junction of the sensing impedance and complex impedance wherein the complex impedance is arranged such that the signal varies proportionally with moisture content and to generate an output value indicative of the moisture content of the medium, the sensing electronics comprising:

a first peak detector circuit connected at the junction of the signal source and the sensing impedance, wherein the first peak detector circuit comprises a first Schottky diode connected in series with a first charging capacitor;

a second peak detector circuit connected at the junction of the sensing impedance and complex impedance, wherein the second peak detector circuit comprises a second Schottky diode connected in series with a second charging capacitor; and a differential amplifier comprising two input terminals, wherein each input terminal is connected at a junction of the first and second Schottky diodes and respective charging capacitors of each peak detector circuit.

* * * * *